United States Patent [19]

Sage, Jr. et al.

[11] Patent Number: 5,320,597

[45] Date of Patent: * Jun. 14, 1994

[54] DEVICE AND METHOD FOR RENEWING ELECTRODES DURING IONTOPHORESIS

[75] Inventors: Burton H. Sage, Jr., Raleigh; Carl R. Bock, Durham, both of N.C.

[73] Assignee: Becton, Dickinson and Company, Franklin Lakes, N.J.

[*] Notice: The portion of the term of this patent subsequent to Aug. 6, 2008 has been disclaimed.

[21] Appl. No.: 652,855

[22] Filed: Feb. 8, 1991

[51] Int. Cl.⁵ ............................................. A61N 1/30
[52] U.S. Cl. ...................................... 604/20; 604/49; 607/149
[58] Field of Search .................. 604/20, 49; 128/798, 128/802, 803

[56] References Cited

U.S. PATENT DOCUMENTS

| | | | |
|---|---|---|---|
| 4,019,510 | 4/1977 | Ellis | 604/20 |
| 4,177,817 | 12/1979 | Bevilacqua | 128/803 |
| 4,383,529 | 5/1983 | Webster | 604/20 |
| 4,406,658 | 9/1983 | Lattin | 604/20 |
| 4,747,819 | 5/1988 | Phipps et al. | 604/20 |
| 4,752,285 | 6/1988 | Petelenz et al. | 604/20 |
| 4,786,278 | 11/1988 | Masaki | 604/20 |
| 4,792,702 | 12/1988 | Masaki | 128/802 |
| 4,886,489 | 12/1989 | Jacobsen | 604/20 |
| 4,942,883 | 7/1990 | Newman | 604/20 |
| 5,006,108 | 4/1991 | LaPrade | 604/20 |
| 5,013,293 | 5/1991 | Sibalis | 604/20 |
| 5,037,381 | 8/1991 | Bock et al. | 604/20 |
| 5,042,975 | 8/1991 | Chien et al. | 604/20 |
| 5,047,007 | 9/1991 | McNichols et al. | 604/20 |

FOREIGN PATENT DOCUMENTS 0230749 8/1987 European Pat. Off. ............. 604/20

Primary Examiner—C. Fred Rosenbaum
Assistant Examiner—Michael Rafa
Attorney, Agent, or Firm—Arthur D. Dawson; Brian K. Stierwalt

[57] ABSTRACT

The present invention provides an iontophoretic drug delivery device having electrode renewing features includes a housing having a first electrode, a second electrode, a circuit for providing electrical communication between the first and second electrodes. The circuit is capable of engaging a source of current. Control means is provided for effecting the amount of current passing between the electrodes. A removable electrolyte reservoir is capable of holding electrolyte and removably engaging the housing so that one of the electrodes can contact electrolyte contained within the reservoir. A removable active agent reservoir is capable of holding an active agent for iontophoretic delivery. The active agent reservoir is capable of removably engaging the housing so that the active agent contacts one of the electrodes.

The present invention also provides a method for renewing electrodes during delivery of an active agent from an iontophoretic system which comprises at least two electrodes and means for containing an active agent, which method comprises:

a) delivering an active agent in connection with a first electrode which completes a circuit with a second electrode in connection with an electrolyte, and b) delivering an active agent from the second electrode by replacing the electrolyte with an active agent in connection with the second electrode and replacing the active agent with an electrolyte in connection with the first electrode.

31 Claims, 3 Drawing Sheets

DEVICE AND METHOD FOR RENEWING ELECTRODES DURING IONTOPHORESIS

FIELD OF THE INVENTION

The invention is in the field of iontophoresis. In particular, the invention relates to new devices and methods for iontophoresis. More particularly, the invention relates to renewing electrodes employed in iontophoresis.

BACKGROUND

Iontophoresis is generally defined as the migration of ions when an electrical current is passed through a solution containing ionized species. The ionized species is usually the ionic form of a drug. The migration of the drug is generally from an iontophoretic system reservoir toward the skin of a patient, and is usually initiated by a small current. Therefore, the most common description of iontophoresis is the delivery of drugs to a patient by the application of electricity.

Iontophoresis provides a noninvasive drug delivery means. When compared to drug delivery by means of a needle, iontophoresis can minimize trauma, pain, infection, and damage.

The primary features of an iontophoresis unit include a battery, a drug reservoir, an indifferent electrolyte reservoir, and usually two electrodes (sometimes referred to as current distribution members which are in contact with the reservoirs). The iontophoresis unit is typically secured to a patient's skin by a fastening means which can include a strap or adhesive means such as adhesive gels. Electrodes are described in a variety of ways but generally include an active electrode and an indifferent electrode. Sometimes the term reservoir system is used to describe an electrode (e.g., reservoir plus electrode). The active electrode has the same charge as the drug to be delivered and the indifferent electrode (also referred to as the return electrode) has a charge opposite the drug to be delivered. For example, if the drug to be delivered to the patient has a positive charge, then the positive electrode will be the active electrode and the negative electrode will serve to complete the circuit. If the drug to be delivered has a negative charge, then the negative electrode will be the active electrode and the positive electrode will be the indifferent electrode. Generally, this can be referred to as a cathode (negative terminal) and anode (positive terminal) electrode system. It is the movement of ions from one electrode to the other electrode that results in the drug being delivered into and through a patient's skin.

Various improvements in iontophoretic methods and devices have been made in the recent past. In particular, many advances have been made in the use and composition of electrodes for iontophoresis. For example, Lattin, U.S. Pat. No. 4,406,658 describes a device in which the polarity of electrodes is reversible. The patent describes an iontophoretic device that permits the iontophoretic process to take place under both electrodes with one application by having a means for switching the polarity of the electrodes. Ellis, U.S. Pat. No. 4,019,510 describes a method for applying low intensity direct current (LIDC) without the detrimental effect of electrical polarization. Another patent, Jacobsen, U.S. Pat. No. 4,886,489, describes a flow through electrode that provides a fresh supply of medicament while taking away the old supply.

In addition, Phipps, U.S. Pat. No. 4,747,819 and Phipps, U.S. Pat. No. 4,744,787 describe improved iontophoretic delivery methods and improved iontophoretic delivery devices, respectively. However, both patents are directed toward teaching how to avoid pH changes and resultant burns to a patient while also increasing drug delivery efficiency. Petelenz, U.S. Pat. No. 4,752,285 also describes methods and devices for iontophoresis which are directed toward avoiding production of competing ions which results in increased efficiency of drug delivery and prevents changes in pH which result in burns to the patient.

However, other than simple replacement, no description or teaching of a device or method for renewing electrodes during iontophoresis has been described.

SUMMARY OF THE INVENTION

The present invention provides a method and a device for renewing electrodes in an iontophoretic system by teaching the use of an active electrode and an indifferent electrode that allows for reversible electrochemistry at each electrode. By teaching a method of renewing the original electrodes, the present invention provides for continued use of an iontophoretic system without the need for electrode replacement. In addition, the known benefits of reduced burns, drug delivery efficiency and the like, obtained with known iontophoretic systems employed are also obtainable in conjunction with the present invention.

The present invention provides an operable iontophoretic drug delivery device having electrode renewing features. The device includes a housing having a first electrode, a second electrode, insulating means for electrically separating the first and second electrodes and circuit means providing for electrical communication between the first and second electrodes. The circuit means is adapted to engage a source of current (including direct current and pulsed current) for providing current between the first and second electrodes. A switch for changing the direction of the current and control means for affecting the amount of current passing between the electrodes is provided. A removable electrolyte reservoir capable of holding electrolyte compositions is provided. The removable electrolyte reservoir is capable of removably engaging the housing so that one of the electrodes can contact electrolyte contained in the electrolyte reservoir. A removable active agent reservoir capable of holding an active agent for iontophoretic delivery is also provided. The active agent reservoir is capable of removably engaging the housing so that the active agent can contact one of the electrodes.

The present invention provides an operable iontophoretic drug delivery device having electrode renewing features including housing means having first electrode contact means, second electrode contact means, insulating means for electrically separating said first and second electrode contact means, and circuit means providing for electrical communication between said first and second contact means. Said circuit means is adapted to engage a source of current for providing current between said first and second electrode contact means. Control means is provided for effecting the amount of current passing between said first and second electrode contact means. A first reservoir includes a first electrode. The first reservoir is adapted to hold an active agent or an electrolyte in contact with the first electrode. The first reservoir is capable of removably engaging said housing so that the first electrode can contact one of said contact means. A removable second reservoir includes a second electrode. The second reservoir is adapted to hold an active agent or an electrolyte in contact with said second electrode. The second electrode reservoir is capable of removably engaging said housing so that said second electrode can contact the other of said contact means.

DETAILED DESCRIPTION OF THE INVENTION

The present invention provides a method for renewing electrodes during delivery of an active agent from an iontophoretic system which comprises at least two electrodes and means for containing an active agent, which method comprises:

a) delivering an active agent in connection with a first electrode which completes a circuit with a second electrode in connection with an electrolyte, and b) delivering an active agent from the second electrode by replacing the electrolyte with an active agent in connection with the second electrode and replacing the active agent with an electrolyte in connection with the first electrode.

The present invention also provides an operable delivery device having electrode renewing features comprising:

housing means including a first electrode, a second electrode, insulating means for electrically separating said first and second electrodes, circuit means providing for electrical communication between said first and second electrodes, said circuit means adapted to engage a source of current for providing current between said first and second electrodes, switch means for changing the direction of said current, and control means for affecting the amount of current passing between said electrodes;

a removable electrolyte reservoir capable of holding electrolyte, said electrolyte reservoir capable of removably engaging said housing so that one of said electrodes can contact electrolyte contained in said reservoir; and a removable active agent reservoir capable of holding an active agent for iontophoretic delivery, said active agent reservoir capable of removably engaging said housing so that said therapeutic liquid can contact one of said electrodes.

The present invention provides the advantages of repeated use of an iontophoretic system without the need for electrode replacement. The elimination of electrode replacement results in added convenience, time savings and monetary savings.

The following terms are defined as used in this document. "Electrode" refers to a substance with the potential for electrochemical activity, which enables an electric current to flow in the presence of an electrolyte. "Anode" refers to an electrode which is positive, toward which negatively charged ions travel. "Cathode" refers to an electrode which is negative, toward which positively charged ions migrate. "Ion" refers to an atom or radical that has lost or gained one or more electrons to acquire an electric charge. "Reduction" refers to the acceptance of one or more electrons by an atom or ion, removal of oxygen from a compound, or addition of hydrogen to a compound. "Oxidation" refers to the loss of one or more electrons by an atom. "Electrolyte" refers to a substance that will provide ionic conductivity. An electrolyte can be solid or liquid. "Active agent" refers to the entity chosen to be delivered by iontophoresis. Thus, active agent refers to the chosen entity and the ionic form of the chosen entity for delivery, such as halide salts of a chosen entity to be delivered (e.g., lidocaine and an ionic form of lidocaine for delivery such as lidocaine hydrochloride). "Reservoir" refers to retaining means for electrical contact with either the electrolyte or the active agent. "Patient" refers to animals, including humans, household animals such as dogs and cats, livestock such as cattle, horses, sheep, pigs, goats and rabbits, laboratory animals such as mice and rats, and zoo animals such as exotic species.

The method is not limited to practice with any one particular iontophoretic system. Any system capable of being replenished with active ingredient and capable of reversing the polarity of the electrode can be used with the method of the invention. Generally, iontophoretic devices comprise at least two electrodes, an electrical energy source (e.g., a battery) and at least one reservoir which contains an agent to be delivered. Several iontophoretic devices are known, such as those disclosed in P. Tyle, *Pharmaceutical Biosearch* 3:318 (1986) and U.S. Pat. No. 4,865,582.

The method of the present invention is exemplified by an iontophoretic system that employs a substantially silver (Ag) electrode as the active electrode (anode) and a substantially silver chloride (AgCl) electrode as the indifferent electrode. An active agent, for example the anesthetic Lidocaine, in its hydrochloride form, is placed in connection with the active silver electrode. An electrolyte, for example saline, is placed in connection with the indifferent silver chloride electrode.

Delivery of active agent is effected by engaging a power source to drive the charged active ingredient from the reservoir in connection with the active electrode into the skin. During iontophoresis, the electrochemical reaction that takes place at the active electrode includes the oxidation of silver atoms which react with the chloride ions from the active agent (e.g., from the Lidocaine hydrochloride) at the silver electrode to form silver chloride. Eventually, the silver electrode becomes a substantially silver chloride electrode. On the other hand, the electrochemistry that takes place at the indifferent electrode includes the reduction of silver chloride which releases a chloride ion into solution, with the eventual result of a substantially silver electrode. After the system has run substantially to exhaustion, the two electrodes have become substantially like the other.

The rate of exhaustion (i.e., the rate of consumption of the electrodes) is determined by the application of Faraday's Law. Faraday's Law is $$\text{mass} = \frac{(MW)(I)(T)}{(Z)(F)}$$

in which
MW is the molecular weight of the electrode composition
I is current applied to the electrode
T is time (measured in seconds)
Z is the valence of the electrode composition
F is 96,500 coulomb/mole
Mass is measured in grams.

From the application of Faraday's Law to the particular iontophoretic system employed, a routine calculation will provide guidance for setting the parameters to run any particular system.

At exhaustion, the active electrode is now substantially silver chloride and the indifferent electrode is now substantially silver. To advantageously utilize this result, the reservoirs under the respective electrodes are switched. In other words, a new reservoir of active agent replaces the electrolyte reservoir and a new reservoir of electrolyte replaces the active agent under the now changed electrodes (but in effect, the reservoirs are still under the same electrode as originally). However, the polarity is still set such that the active electrode is now the silver chloride electrode and the indifferent electrode is now the silver electrode. To correct this, and arrive at a system with the original active and indifferent electrodes, the polarity of the electrodes are changed. The polarity reversal can be effected by a switching means or by having the electrode detachable with the reservoirs so that the polarity remains the same but the electrodes are switched. The change of electrode polarity can occur either before or after the reservoirs are switched. That is, the original silver electrode (now the silver chloride electrode) is now the indifferent electrode and the original silver chloride electrode is now the active silver electrode. Therefore, the system is now ready to run as it was originally set up. The active electrode is still the silver electrode and the indifferent electrode is still the silver/silver chloride electrode. In other words, the system is now ready to drive the active ingredient out of the reservoir connected with the active electrode. In addition, the electrodes have been renewed for use a second time, this time as the opposite electrode for which they were used the first time. In principle, this process can continue indefinitely.

The method of the invention is particularly advantageous in view of the fact that reversing polarity, alone, actually results in delivery of active agent in less amounts than no polarity reversal (i.e., delivery from only one reservoir).

The ability to use one electrode and then the other as first the active electrode and then the indifferent electrode is significant. The foremost advantage is the continued use of an iontophoretic system without the need for electrode replacement. Not only does the elimination of electrode replacement result in saving time, but the elimination of electrode replacement also results in saving expenses. Electrodes like those made of precious metals are usually expensive, adding considerable expense to the maker and eventual user of an iontophoretic device that employs such electrodes. Therefore, the method of the present invention not only provides for repeated use of the same electrode, but provides a time saving method and a cost saving method for iontophoresis. The present invention provides a method for renewing the electrode surfaces in an iontophoretic system by teaching the use of an active electrode and an indifferent electrode that takes advantage of reversible electrochemistry at each electrode.

Although the invention has been described with silver and silver chloride electrodes, there are other suitable electrodes that allow for reversible chemistry that can be employed. Known electrochemical reactions can be found in texts such as CRC Handbook of Chemistry and Physics, 68th edition, CRC Press, Inc. (1987-1988), Boca Raton, Florida, at pages D-151 to D-158. For example, the halide on the surface of the silver/silver chloride electrode can be any of the halogens such as iodine, bromine and fluorine, besides chlorine. Preferably the halogen is chlorine or bromine. Likewise, other electrodes can comprise gold, copper, molybdenum, lead and certain metals in groups one, two, and three, of the periodic table, which react with compounds in groups five, six, and seven, of the periodic table, such that the potential of the reaction in aqueous solution is less than about 1.0 volt and the salt created by the reaction is essentially insoluble. Preferably the electrode is silver or gold. For example, the following electrodes and electrochemistry can be used with the present invention:

| Active Electrode | Indifferent Electrode |
| --- | --- |
| $Ag + Cl^- \rightarrow AgCl + e^-$ | $AgCl + e^- \rightarrow Ag + Cl^-$ |
| $Ag + Br^- \rightarrow AgBr + e^-$ | $AgBr + e^- \rightarrow Ag + Br^-$ |
| $Ag + I^- \rightarrow AgI + e^-$ | $AgI + e^- \rightarrow Ag + I^-$ |
| $Ag + F^- \rightarrow AgF + e^-$ | $AgF + e^- \rightarrow Ag + F^-$ |
| $Pb + 2Cl^- \rightarrow PbCl_2 + 2e^-$ | $PbCl_2 + 2e^- \rightarrow Pb + 2Cl^-$ |
| $2Pb + SO_4^{2-} \rightarrow Pb_2SO_4 + 2e^-$ | $Pb_2SO_4 + 2e \rightarrow Pb + SO_4^=$ |

Electrodes can be in the form of a wire, mesh or printed ink. The actual form of the electrode is not critical to the invention. Active electrodes are preferably chosen for their ability to react with complementary ions of the active agent. Also, the active electrodes preferably react at potentials in aqueous solutions less than about one volt (the electrolysis of water) and form insoluble salts with the complementary ion of the active agent. Such electrodes are oxidized or reduced during operation of the iontophoretic device and produce a species which reacts with ions present in solution to form a relatively insoluble salt or compound. The active agent is typically in the form of a salt, base or acid prior to delivery. Preferably the ions of the electrode (i.e., reactive or consumable electrode) and the ions complementary to the active agent (i.e., the ion which forms the salt with the active agent) form a relatively insoluble precipitate. Such ions include ions of sodium, potassium, chloride and sulfate. The formation of insoluble precipitates minimizes ion competition with the active agent to be delivered. The use of reactive electrodes in the present invention (i.e., noninert) also eliminates the electrolysis of water. Electrolysis of water in an iontophoretic system involves an oxidative reaction near the anode which produces hydronium ions (H+) and reductive reaction near the cathode which produces hydroxyl ions (OH−). Production of H+ and OH− ions are generally believed to contribute to burns to the patient. Therefore, proper selection of electrodes, active agent, and form of active agent are taken into account when choosing the proper iontophoretic setup.

Adverting to FIGS. 1 through 4, an operable iontophoretic delivery device 20 having electrode renewing features includes a housing having a first electrode 22 and a second electrode 23 electrically separated by insulating material 25.

For the purposes of the description of the present invention, the term "proximal" or "lower" is meant to refer to the side of the device closest to the patient's skin, whereas the term "distal" or "upper" is meant to refer to the side of the device or element which is furthest from the patient's skin.

Figure 4:
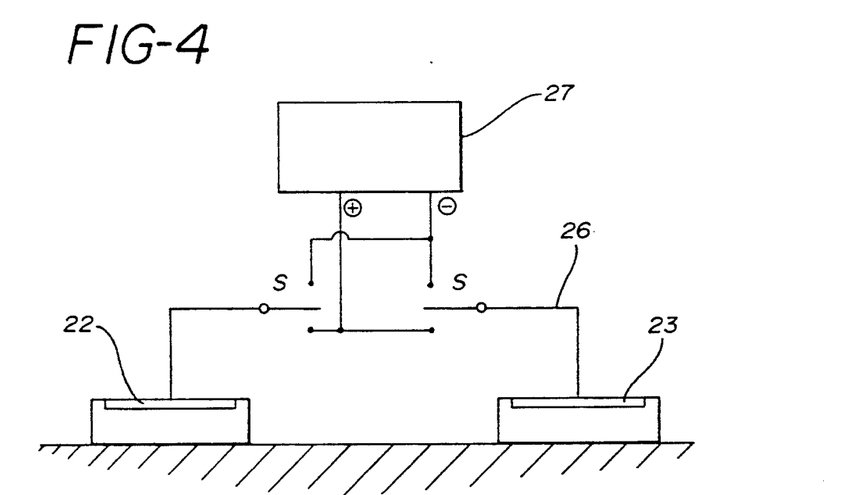
FIG. 4 is a schematic view showing a circuit for providing current between the electrodes.

The housing contains circuit means for providing electrical communication between said first and said second electrodes. A representative circuit 26 is illustrated in FIG. 4. In the preferred embodiment, circuit 26 is adapted to removably engage a source of current, such as a battery 27 for providing current between the electrodes. Switch means "S" is provided for changing the direction of the current between the electrodes. A control means is provided for regulating the amount of current passing between the electrodes. The control means may consist of an on/off switch, simple control devices such as a rheostat or more complex interactive control devices which are well known in the art. An activator control 28 is provided for the control means. Control means are capable of controlling current including maintaining a constant current to the electrodes and/or controlling voltage and power including maintaining a constant voltage between the electrodes and maintaining a constant power to the electrode. Some of the many control devices and circuits in the prior art are taught in U.S. Pat. No. 4,292,968 to Ellis, U.S. Pat. No. 4,822,334 to Tapper, U.S. Pat. No. 3,991,755 to Vernon et al. and U.S. Pat. No. 4,725,263 to McNichols et al.

Figure 1:
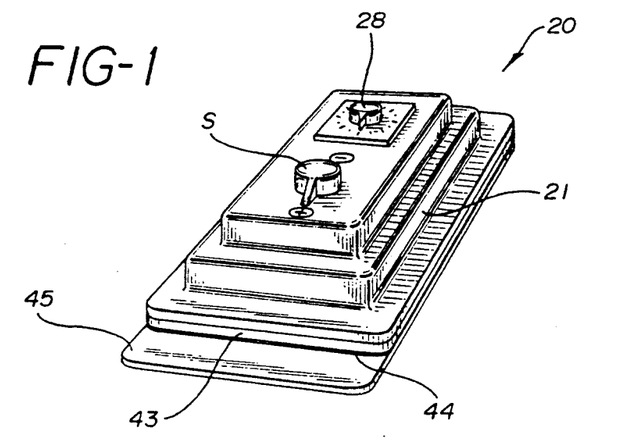
FIG. 1 is a perspective view of the iontophoretic drug delivery device of the present invention.
Figure 2:
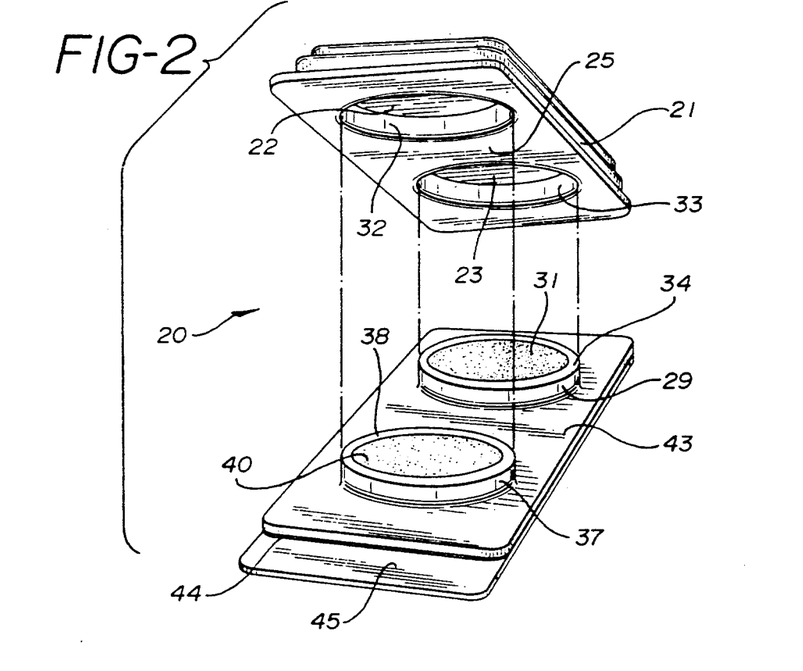
FIG. 2 is a perspective view of the drug delivery device of FIG. 1 illustrating the separation of the housing and the reservoirs.
Figure 3:
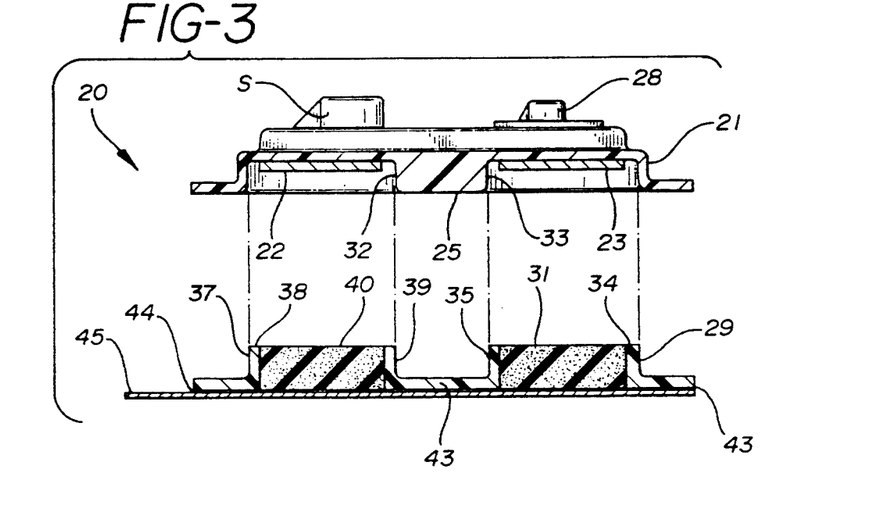
FIG. 3 is a partial cross-sectional view of the iontophoretic delivery device of FIG. 1 taken along line 3—3, and also showing the separation of the housing and the reservoirs.

A removable electrolyte reservoir 29 is capable of holding electrolytes such as electrolyte 31. The electrolyte reservoir is capable of removably engaging the housing so that electrolyte contacts either first electrode 22 or second electrode 23. In this embodiment, the housing includes circular recess 32 adjacent to first electrode 22 and circular recess 33 adjacent to second electrode 23. Electrolyte reservoir 29 includes distal or upper end 34 having circular engaging surface 35. The diameter of circular engaging surface 35 is slightly larger than the diameter of circular recesses 32 and 33 so that the electrolyte reservoir may be frictionally and removably engaged with the housing by gently forcing it into one of the circular recesses. For example, as illustrated in FIG. 3 electrolyte reservoir can be engaged with circular recess 33 so that the electrolyte 31 contacts second electrode 23. Electrolyte reservoir 29 may also engage circular recess 32 so that the electrolyte contacts first electrode 22.

A removable active agent reservoir 37, capable of holding an active agent such as active agent 40, includes distal or upper end 38 having a circular engaging surface 39 thereon. Circular engaging surface 39 of removable active agent reservoir 37 is capable of frictionally engaging either circular recess 32 or circular recess 33 in the housing so that active agent 40 can contact either first electrode 22 or second electrode 23. In FIG. 3, removable active agent reservoir 37 is shown in alignment with and for engagement with circular recess 32 so that the active agent contacts first electrode 22.

The instant embodiment also contains alignment member 43 capable of holding the electrolyte reservoir and the active agent reservoir in a spaced relationship for alignment and engagement with housing 21. Because of the symmetry of the reservoirs the reservoir and alignment assembly can be engaged either with the active agent reservoir in communication with first electrode 22 or in communication with second electrode 23.

Alignment member 43 also contains a coating of adhesive 44 on its proximal side. A release sheet 45 is provided to protect the adhesive before time of use and for helping to contain the active agent and the electrolyte in the reservoirs before time of use. At time of use, the reservoirs are engaged with the housing so that one electrode is in contact with the active agent and the other electrode is in contact with the electrolyte. For example, first electrode 22 contacts the active agent and second electrode 23 contacts the electrolyte. The release sheet 45 is then removed from the adhesive backed alignment member and the iontophoretic device 20 is pressed against the skin of the patient. The switch "S" is positioned so that the charge on first electrode 22 is identical to the charge of the active agent being delivered to the patient. For example, switch "S" should be used to direct current toward first electrode 22 and provide a positive charge to electrode 22 if the active agent being delivered has a positive charge such as Lidocaine hydrochloride. Activator control 28 is then set to start the delivery process. As taught herein, a silver electrode may be used to combine with the chloride in the Lidocaine hydrochloride so that throughout the process of delivering the Lidocaine th electrode will change from substantially silver to substantially silver chloride. Also, second electrode 23 may be made substantially of silver chloride so that throughout the delivery process, as described herein, the second electrode will gradually change toward being a substantially silver electrode.

After the active agent is delivered, causing changes to the electrodes, the iontophoretic delivery device 20 may be removed from the patient's skin and the alignment member containing both reservoirs may be removed from the housing and discarded. A new alignment member containing fresh active agent such as Lidocaine hydrochloride and fresh electrolyte such as saline may now be installed in the housing. However, at this time, the electrolyte reservoir 29 will be engaged with circular recess 32 so that the electrolyte contacts the first electrode which has changed to substantially silver chloride and the active agent reservoir 37 will be engaged with circular recess 33 so that the active agent contacts second electrode 23. The backing sheet on the new alignment member may now be removed so that the iontophoretic delivery device may be placed on the patient's skin. At this time, switch "S" is positioned to reverse the flow of current toward second electrode 23 so that the second electrode 23 achieves a positive charge to drive the active agent into the patient's skin. Activator control 28 is then set to start the delivery process. As the process proceeds electrode 23 will convert back from substantially silver to substantially silver chloride surface and electrode 23 will convert back from substantially silver chloride to substantially silver. The process described hereinabove may be reversed many times thereby constantly renewing electrodes which would otherwise lose their ability to deliver medication after a limited amount of use. The present invention also allows the use of less electrode material since the electrodes are constantly being renewed This embodiment is being described as delivering a positively charged active agent into the patient's skin. The instant invention can also be used to drive a negatively charged active agent in to the patient's skin by placing the reservoir containing the active agent so that the active agent contacts the negatively charged electrode and the electrolyte contacts the positively charged electrode.

The embodiment illustrated in FIGS. 3 and 4 incorporates switch means for reversing the current coupled with replaceable active agent and electrolyte reservoirs. It is also within the purview of the instant invention to include embodiments having a housing without a switch means wherein the separate reservoirs contain the electrode and are manually fillable. In this alternative embodiment an assembly including the reservoirs and the electrodes can be removed from the housing and each reservoir being alternately filled with electrolyte or active agent at the end of each drug delivery cycle. The same result will be achieved in that the electrodes will be constantly renewed by being in contact with electrolyte or therapeutic liquid. Between each cycle, the reservoirs, including the electrodes will be placed on different sides of the housing so that the current will be alternated between delivery cycles by placement of the electrodes with respect to the housing rather than an internal switching system.

A wide variety of materials is suitable for the housing with plastic material such as polystyrene, polyethylene, polypropylene and ABS being preferred. The housing may also be constructed of metal however plastic is preferred because it can function as an insulating material between the electrodes.

Electrical components such as thermistors, wires, switches, and circuit boards containing commercially available custom circuit chips are readily available for constructing an iontophoretic delivery device.

The reservoir or similar structure that contains the active agent to be delivered can be in the form of any material suitable for making contact between the iontophoresis unit and the skin. Suitable materials include, but are not limited to foams such as disclosed in U.S. Pat. No. 4,820,525 to T. W. Leonard et al., ion exchange resins such as disclosed in U.S. Pat. No. 4,731,049 to E. J. Pursi, gels such as disclosed in U.S. Pat. No. 4,706,680 to P. Keusch and 4,474,570 to S. Ariura, and matrices such as those disclosed in U.S. Pat. No. 4,702,732 to N. R. Powers. Preferably the active agent is contained in a rigid reservoir of material suitable for engaging the housing such as thermoplastic material. Examples of thermoplastic materials are polypropylene, polyethylene and polystyrene.

Iontophoresis gels for use as reservoir materials and/or adhesive means can be karaya gum, other polysaccharide gels, or similar hydrophillic aqueous gels capable of carrying ions. Specific examples of such gels include polyvinyl alcohol, polyvinyl pyrrolidone, methylcellulose, polyacrylamide, polyhemas, polyhema derivatives and the like.

The reservoir material selected to hold the active agent should have nonirritating properties to avoid irritating the person's skin or tissue, suitable surfactant properties to hold the active agent formulation, provide good electrical contact between the skin and the active agent formulation, and the ability to act as a carrier medium for the ions without interfering with the desired properties of the active agent to be delivered.

Suitable electrolytes for use in the present invention include saline and aqueous solutions of halide salts such as calcium chloride, potassium chloride, potassium gluconate, sodium chloride and sodium lactate. Preferably the electrolyte is sodium chloride or saline. The primary criteria for selection of an electrolyte is the ability for it to safely provide ionic conductivity.

The term "active agent" as used to describe the principal active ingredient for use in the methods and devices of the invention refers to a biologically active compound or mixture of compounds that has a therapeutic, prophylactic or other beneficial pharmacological and/or physiological effect on the recipient patient and is sufficiently potent such that it can be delivered through the skin or other membrane to the recipient in sufficient quantities to produce the desired result.

The active agent for use in the method of the invention can be delivered alone, as a prodrug, or in combination with other substances. Other substances can include permeation enhancers, buffers, bacteriostatics, stabilizers, antioxidants, and other agents whose role is to enhance the therapeutic action, shelf life, safety, and useability.

In general, active agents include therapeutic agents, or combinations thereof, in all of the major therapeutic areas including, but not limited to, anesthetics, analgesics, anorexics, anthelmintics, antiasthma agents, anticonvulsants, antidiarrheals, antimigraine preparations, antimotion sickness, antinauseants, antieoplastics, antiparkinsonism drugs, antipruritics, antipyretics, anticholinergics, sympathomimetics, xanthine derivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decogestants, diagnostics, hormones, hypnotics, immunosuppressives, muscle relaxants, parasympatholytics, parasympathomimetics, psychostimulants, sedatives, tranquilizers, antiinflammatory agents, antiarthritic agents, antispasmodics, antidepressants, antipsychotic agents, tranquilizers, antianxiety agents, narcotic antagonists, antiparkinsonism agents, cholinergic agonists, anticancer agents, immunosuppression agents, antiviral agents, antibiotic agents, appetite suppressants, antiemetics, anticholinergics antihistamines, antimigraine agents, coronary, cerebral or peripheral vasodilators, hormonal agents, contraceptive agents, antithrombotic agents, diuretics, antihypertensive agents, cardiovascular drugs and the like. Examples of specific drugs are steroids such as estradiol, progesterone, norgestrel, levonogestrel, norethindrone, medroxyprogestrone aceate, testosterone and their esters, nitro compounds such as nitroglycerine and isosorbide nitrates, nicotine, chlorpheniramine, terfenadine, triprolidine, hydrocortisone, oxicam derivatives such as piroxicam, ketoprofen, mucopolysaccharidases such as thiomucase, buprenorphine, fentanyl, naloxone, codeine, lidocaine, dihydroergotamine, pizotiline, salbutamol, terbutaline, prostaglandins such as misoprostol and enprostil, omeprazole, imipramine, benzamides such as metoclopramine, scopolamine, peptides such as growth releasing factor and somatostatin, clonidine, dihydropyridines such as nifedipine, verapamil, ephedrine, pindolol, metoprolol, spironolactone, nicardipine hydrochloride, calcitriol, thiazides such as hydrochlorothiazide, flunarizine, sydononimines such as molsidomine, sulfated polysaccharides such as heparin fractions and proteins and peptides such as insulin and analogs thereof, calcitonin and analogs thereof such as elcatonin, protamine, glucaqon, globulins, angiotensin I, angiotensin II, angiotensin III, lypressin, vasopressin, somatostatin and its analogs, growth hormones, and oxytocin, and the salts of such compounds with pharmaceutically acceptable acids or bases, as may be required. Preferably the active agent is an anesthetic, hormone, protein, analgesic, or other low molecular weight cations. More preferably the active agent is lidocaine, insulin, calcitonin, elcatonin or somatostatin.

Primary requirements of an active agent are that it be charged, capable of modification to carry a charge or complexed with another compound so that the complex has a charge (e.g., by hydrophobic interactions). Appropriate selection of active agents for iontophoretic applications include a selection based on specific conductivity (i.e., estimates how easily drugs move in solution when an electric current is applied).

Active agent modification for iontophoretic delivery is guided by well-known procedures. General texts in the field include *Remington's Pharmaceutical Sciences*, Ed. Arthur Osol, 16th ed., 1980, Mack Publishing Co., Easton, Pa. Typically the basic ($OH^-$ or amine) or acid ($H^+$) form of the active agent is made, depending on whether the anionic (negative charged ion) or cationic (positive charged ion) form of the active agent is to be delivered. Common modifications of active agents include modification to a halide salt form. For example, to deliver a positively charged active agent, the chloride or hydrochloride form of the active agent is made and placed in the iontophoretic device reservoir for delivery.

An effective amount of active agent means that amount needed to produce the intended result following its iontophoretic administration. The effective amount will vary, depending, among other factors, on the physiological effect desired, the frequency of administration, active agent and intradermal metabolism.

The treatment regimen for use in the present invention includes the consideration of a variety of factors, including the type, age, weight, sex, medical condition of the patient, severity of the condition and active agent to be delivered. An ordinarily skilled physician can readily determine, prescribe, and administer the effective amount of the agent required to prevent or arrest the progress of the condition. In so proceeding, the physician could employ relatively low doses at first and subsequently increase the dose until a maximum response is obtained.

The following examples illustrate the specific embodiments of the invention described in this document. As would be apparent to skilled artisans, various changes and modifications are possible and are contemplated within the scope of the invention described.

EXAMPLE I

Figure 5:
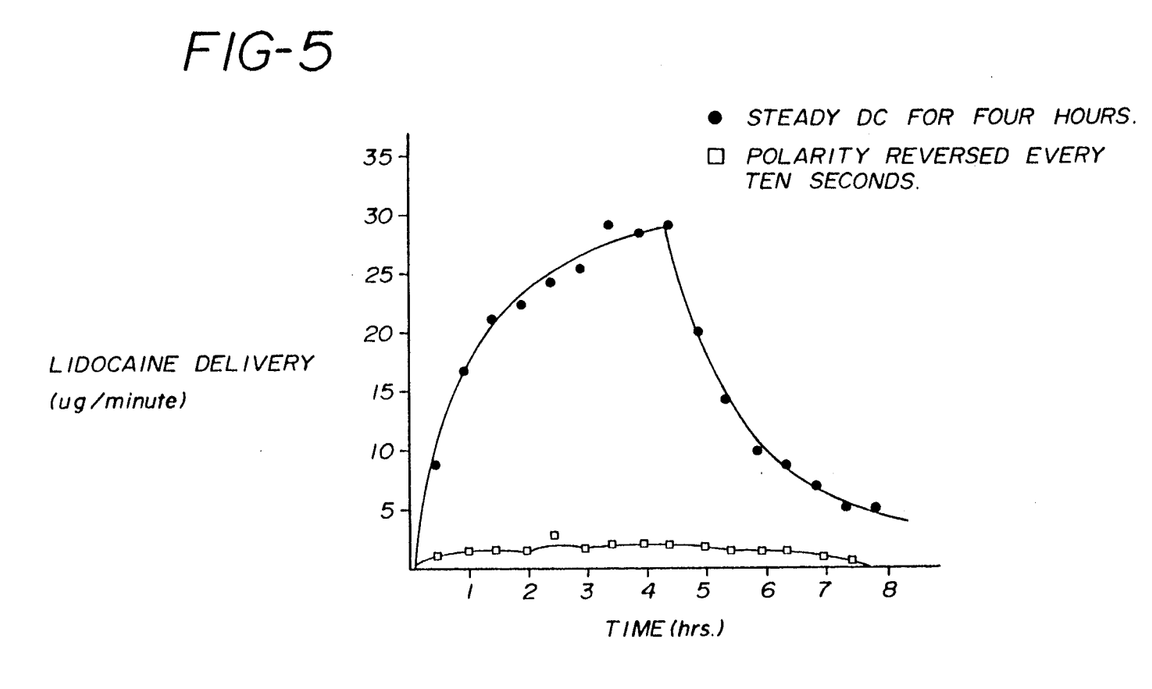
FIG. 5 shows active agent delivery is more effective at steady direct current than with polarity reversal.

The following Example and FIG. 5 illustrate that switching polarity alone, actually delivers less active ingredient than a system not reversing polarity The porcine skin flap test is performed in substantial accordance with the procedures described in J. E. Riviere, B. H. Sage and N. A. Monteiro-Riviere (1989-90) "Transdermal Lidocaine Iontophoresis in Isolated Perfused Porcine Skin," *J. Toxicol—Cut and Ocular Toxicol* 8(4) p 493-504, incorporated herein by reference.

The following changes are made in the protocol:
Active electrode—10% lidocaine HCl+0.04% tolozoline HCl
Indifferent electrode—normal saline or 10% saline
Current density—200$\mu$A/cm$^2$
Electrochemistry—Ag/AgCl
Skin flaps 241-244—steady direct current for 4 hours
Skin flaps 512,513—polarity reversed every 10 seconds.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. An operable iontophoretic delivery device having electrode renewing features comprising:
   housing means including a first electrode, a second electrode, insulating means for electrically separating said first and second electrodes, circuit means providing for electrical communication between said first and second electrodes, said circuit means adapted to engage a source of current for providing current between said first and second electrodes, switch means for changing the direction of said current, and control means for affecting the amount of current passing between said electrodes;
   a removable electrolyte reservoir capable of holding electrolyte, said electrolyte reservoir capable of removably engaging said housing so that one of said electrodes can contact electrolyte contained in said reservoir; and
   a removable active agent reservoir capable of holding an active agent for iontophoretic delivery, said active agent reservoir capable of removably engaged said housing so that said active agent can contact one of said electrodes.

2. The operable iontophoretic delivery device of claim 1 wherein said source of current is a battery.

3. The operable iontophoretic delivery device of claim 2 wherein said battery is contained within said housing means.

4. The operable iontophoretic delivery devide of claim 1 wherein said electrodes are selected from the group consisting of silver, silver halides, gold, gold halides, copper, copper halides, molybdenum and molybdenum halides.

5. The operable iontophoretic delivery device of claim 4 wherein one of said electrodes is silver.

6. The operable iontophoretic delivery device of claim 4 wherein one of said electrodes is silver chloride.

7. The operable iontophoretic delivery device of claim 4 wherein said electrodes are silver chloride and silver.

8. The operable iontophoretic delivery device of claim further including holding means for holding said electrolyte reservoir and said active agent reservoir in spaced relationship so that both reservoirs may be simultaneously removably connected to said housing with either reservoir aligned with either electrode.

9. The operable iontophoretic delivery device of claim 8 further including adhesive for holding said reservoirs adjacent to the skin of a patient.

10. The operable iontophoretic delivery device of claim 9 including a removable release sheet for covering said adhesive before the time of use and for covering said reservoirs.

11. The operable iontophoretic delivery device of claim 1 wherein said control means includes means for maintaining a constant current between said first and second electrodes.

12. The operable iontophoretic delivery device of claim 1 wherein said control means includes means for maintaining a constant voltage between said first and second electrodes.

13. The operable iontophoretic delivery device of claim 1 wherein said active agent reservoir contains a therapeutic agent.

14. The operable iontophoretic delivery device of claim 13 wherein said therapeutic agent is selected from the group consisting of insulin, calcitonin, lidocaine, somatostatin, elcatonin, and the ionic forms thereof.

15. An operable iontophoretic drug delivery device having electrode renewing features comprising:
    housing means including a first electrode contact means, a second electrode contact means, insulating means for electrically separating said first and said second electrode contact means, circuit means providing for electrical communication between said first and second contact means, said circuit means adapted to engage a source of current for providing current between said first and second electrode contact means, and control means for affecting the amount of current passing between said first and second electrode contact means;
    a removable first reservoir including a first electrode, said first reservoir adapted to hold an active agent or an electrolyte in contact with said first electrode, said first reservoir capable of removably engaging said housing so that said first electrode can contact one of said contact means; and
    a removable second reservoir including a second electrode, said second reservoir adapted to hold an active agent or an electrolyte in contact with said second electrode, said second reservoir capable of removably engaging said housing so that said second electrode can contact the other of said contact means.

16. The operable iontophoretic delivery device of claim 15 further including adhesive on said first and second reservoirs for holding said reservoirs adjacent to the skin of a patient.

17. The operable iontophoretic device of claim 16 including a removable release sheet for covering said adhesive before time of use and for covering said reservoirs.

18. A method for renewing electrodes during delivery of an active agent from an iontophoretic system which comprises at least two electrodes and means for containing an active agent, which method comprises:
    a) delivering an active agent in connection with a first electrode which completes a circuit with a second electrode in connection with an electrolyte, and
    b) delivering an active agent from the second electrode by replacing the electrolyte with an active agent in connection with the second electrode and replacing the active agent with an electrolyte in connection with the first electrode.

19. The method of claim 18 in which the delivery of the active agent is from a cathode.

20. The method of claim 18 in which the delivery of the active agent is from an anode.

21. The method of claim 18 in which the electrodes are metals and their salts which have reversible electrochemistries with an interface potential less than that required for electrolysis of water.

22. The method of claim 21 in which the electrodes are selected from the group consisting of silver, silver halides, gold, gold halides, copper, copper halides, molybdenum and molybdenum halides.

23. The method of claim 22 in which the electrodes are silver and silver chloride.

24. The method of claim 18 in which the active agent is selected from the group consisting of insulin, calcitonin, lidocaine, somatostatin, elcatonin, and the ionic forms thereof.

25. The method of claim 23 in which the active agent is lidocaine.

26. The method of claim 18 in which the electrolyte is selected from the group consisting of active agent, saline, and aqueous solutions of halide salts.

27. The method of claim 26 in which the electrolyte is saline.

28. The method of claim 26 in which the electrolyte is an aqueous solution of halide salts.

29. The method of claim 18 in which delivery of active agent from the second electrode is effected by a switching means.

30. The method of claim 18 in which the electrodes are silver and silver chloride and the electrolyte is saline.

31. The method of claim 18 in which the electrodes are silver and silver chloride, the electrolyte is saline, and the active agent is lidocaine hydrochloride.

* * * * *